(12) United States Patent
Maschke

(10) Patent No.: US 8,535,230 B2
(45) Date of Patent: Sep. 17, 2013

(54) ULTRASOUND DEVICE

(75) Inventor: Michael Maschke, Lonnerstadt (DE)

(73) Assignee: Siemens Aktiengesellschaft, München (DE)

(*) Notice: Subject to any disclaimer, the term of this patent is extended or adjusted under 35 U.S.C. 154(b) by 506 days.

(21) Appl. No.: 12/284,945

(22) Filed: Sep. 26, 2008

(65) Prior Publication Data
US 2009/0088639 A1 Apr. 2, 2009

(30) Foreign Application Priority Data
Sep. 28, 2007 (DE) .......................... 10 2007 046 700

(51) Int. Cl.
*A61B 8/00* (2006.01)
(52) U.S. Cl.
USPC .......................................... 600/443; 600/437
(58) Field of Classification Search
USPC ............ 600/437, 443, 459; 700/245; 901/14
See application file for complete search history.

(56) References Cited

U.S. PATENT DOCUMENTS

| 4,807,273 | A | 2/1989 | Haendle | |
|---|---|---|---|---|
| 5,002,173 | A * | 3/1991 | Hucul et al. | 192/150 |
| 5,817,022 | A | 10/1998 | Vesely | |
| 5,878,112 | A | 3/1999 | Koertge | |
| 6,246,898 | B1 * | 6/2001 | Vesely et al. | 600/424 |
| 6,425,865 | B1 * | 7/2002 | Salcudean et al. | 600/437 |
| 6,770,034 | B2 | 8/2004 | Sunagawa et al. | |
| 7,753,851 | B2 * | 7/2010 | Nilsson | 600/459 |
| 2008/0021317 | A1 * | 1/2008 | Sumanaweera | 600/437 |
| 2008/0240363 | A1 | 10/2008 | Grebner et al. | |
| 2010/0041991 | A1 * | 2/2010 | Roundhill | 600/443 |

FOREIGN PATENT DOCUMENTS

| DE | 3146543 | A1 | 6/1983 |
|---|---|---|---|
| DE | 3636678 | A1 | 5/1988 |
| DE | 4029581 | A1 | 3/1992 |
| DE | 19625409 | A1 | 1/1998 |
| DE | 69831138 | T2 | 12/1999 |
| DE | 102005012700 | A1 | 9/2006 |
| WO | 2006043859 | A1 | 4/2006 |

\* cited by examiner

*Primary Examiner* — Michael Rozanski

(57) ABSTRACT

An ultrasound device is provided. The ultrasound device includes an ultrasound transducer to be moved along an object to be examined and a control device that communicates with the ultrasound device, controls the transmit and receive mode of the ultrasound transducer and processes the ultrasound signals received. The ultrasound transducer is arranged on a robotic arm that can be freely moved in space and controlled in terms of its movement.

13 Claims, 1 Drawing Sheet

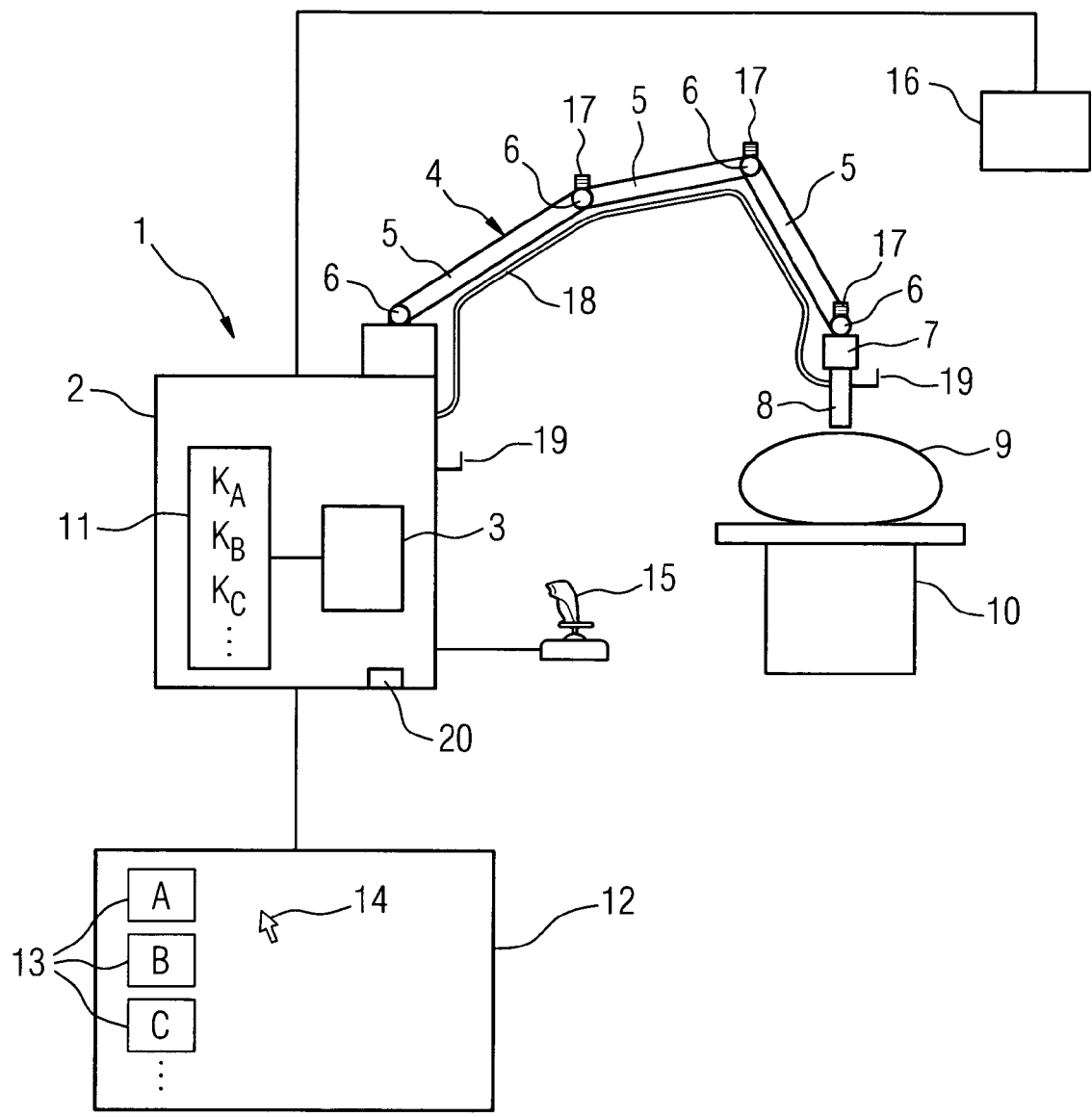

ULTRASOUND DEVICE

CROSS REFERENCE TO RELATED APPLICATIONS

This application claims priority of German application No. 10 2007 046 700.3 filed Sep. 28, 2007, which is incorporated by reference herein in its entirety.

FIELD OF INVENTION

The invention relates to an ultrasound device comprising an ultrasound transducer that is to be moved along an object to be examined and a control device that communicates with said ultrasound device, controls the transmit and receive mode of the ultrasound transducer and processes the ultrasound signals received.

BACKGROUND OF INVENTION

Medical imaging is necessary to diagnose a large number of diseases. The oldest method, die X-ray technology, delivers high-resolution images within a short examination time, however, it has the disadvantage of exposing the patient to X-rays. Ultrasound imaging is a method of image acquisition that works without using radiation. With said ultrasound imaging, ultrasound signals are sent via an ultrasound transducer into the object to be examined and a corresponding control device receives the reflected ultrasound signals and processes the receive signals for imaging purposes.

SUMMARY OF INVENTION

The advantage of such an ultrasound examination is the short examination time, the adequate resolution and the use of sound waves that are not harmful to biological tissue. However, in order to obtain highly diagnostic images, it is essential that the ultrasound transducer that the doctor or medical personnel manually moves and positions on the patient's skin, is placed and guided with great precision. As not every operator has the appropriate experience in using the ultrasound transducer that is to be moved manually, there is the problem that despite in principle there being the possibility of recording images that show, for example, actually existing pathological findings, this is not recognized, as, as a consequence of the ultrasound transducer not being optimally guided, the relevant area was not recorded or not recorded with a sufficiently high diagnostic representation.

The invention is, therefore, based on the problem of presenting an ultrasound device that in principle allows improved guiding of the ultrasound transducer.

In order to solve this problem, an ultrasound device of the inventive type provides for the ultrasound transducer to be arranged on a robotic arm whose movement can be controlled and can freely move in space.

Contrary to previous standard practice, with the ultrasound device according to the invention, the operator no longer moves the ultrasound transducer. The movement of the ultrasound transducer is carried out by a robotic arm, which can be moved in space by at least three degrees of freedom, preferably six degrees of freedom. The more movable the robotic arm, the better the directional positioning of the ultrasound transducer that can be achieved by the corresponding arm control. In one embodiment of the robotic arm, by way of example as multi-articulated arm, which can be moved by six degrees of freedom, all longitudinal movements and also rotations around all spatial axes are possible, so that the ultrasound transducer can be moved to each position in the available movement capacity.

The use of a controlled robotic arm offers the possibility of automating the movement of the ultrasound transducer, so that the operator thus no longer has to move the head himself and search for the corresponding image acquisition positions, incurring the risk of not going to specific relevant positions, and hence not recording any images from there. Rather using the robot, it is possible for the movement operation of the ultrasound transducer to be controlled and automated, which can ensure that all relevant areas are actually captured and all the relevant image acquisition positions are covered.

Thereby in a practical development, several separate selectable control curves defining movement paths are stored in the central control device of the ultrasound device or an additional control device, by means of which the movement of the robotic arm can be controlled. Thus the control device has at its disposal an assemblage of separate control curves, which define the movement paths of the ultrasound transducer along the patient. The individual control curves, which are defined using a plurality of movement parameters or control parameters or define corresponding parameters, are selectable, i.e., the operator can select the appropriate control curve for him as required.

Thereby, in a particularly practical embodiment of the invention, at least one part of the control curve, preferably all control curves, are assigned to specific examination areas or organs of the object to be examined. That means that area or organ-specific control curves, which define the optimal area or organ-specific movement paths, are stored for the image acquisition of specific examination areas or specific organs. This ensures that for each examination area or for each organ there is an optimal movement path and hence an optimal image acquisition at all-important positions and from all important transducer orientations.

To simplify the selection of the required control curve for the operator, for practical purposes a selection device is provided, by means of which it is possible to select an examination area or an organ and hence the control curve assigned for use in the examination of the said organ or area. A display screen is conceivable for instance, on which specific examination areas (e.g. thyroid, pancreas, liver, etc.) are indicated by different icons or in written form. The operator can then use the screen cursor to select the desired examination area or the desired organ, whereupon at the control device, the control curve assigned to the area or organ is automatically selected and subsequently followed in the course of the image acquisition.

For practical purposes, the control device for creating a control curve is designed in such a way that a manual or controlled movement of the ultrasound transducer located on the robotic arm is detected and stored as a control curve. An experienced operator thus follows an area or organ-specific movement path one or several times, when he correspondingly guides the robotic arm switched to "idle" with respect to its drive devices, which arm is thus manually freely movable, together with the ultrasound transducer and travels the complete movement path with the ultrasound transducer, and this, based on his experience, ensures optimal scanning of the entire area occurring. The control device is now able to detect the entire movement path, which for practical purposes using one or several sensors provided on the robotic arm, which capture the information describing the arm movement, which information is used to create the control curves. Such sensors can be, for example, position, path or angle sensors, which describe the positioning and movement of the arm correspondingly. Using the path describing signals picked up in the process, the control device can now determine the corresponding control curve, in order subsequently to guide the robotic arm or its individual drive devices on the arm joints in such a way that the ultrasound transducer is guided exactly according to the movement path once traveled manually by the operator. To this end the control device can have, for example, a neural network or other self-learning application software.

In addition to the automatic arm movement via control curves it is in principle also possible, to control the movement of the robotic arm via a manually operated control device, in particular a joystick, whereby the control device is designed in such a way as to move the robotic arm three-dimensionally in space. This makes it possible, for example, without manual movement of the ultrasound transducer itself, to move said ultrasound transducer into an optimal start position, from which the automated arm and ultrasound transducer movement then occurs after selection of the corresponding control curve.

In addition, for practical purposes, means are provided on the robotic arm to prevent the ultrasound transducer placing inadmissible pressure on the object to be examined, this prevents the transducer being pressed too hard on the object to be examined, causing the patient either to feel pain for a brief moment or to be injured. Such means can comprise at least one force sensor and/or safety clutches in the region of arm joints. Through the means, regardless of what kind, an electronic control can carry out or if need be also stop the arm movement so that no inadmissibly high pressure occurs or so that, if the pressure were to rise inadmissibly, the movement would be stopped immediately and possibly reversed. Thus if, for example, several force sensors are used on the arm, then said sensors provide corresponding signals regarding any increase in force. The electronic control can then alter the speed of movement etc. Here it is also possible to make a corresponding optimization of the respective control curve in relation to the respective object to be examined. For example, if the ultrasound transducer is travelling over the abdominal wall, then the respective movement path in the case of a patient with a flat abdomen is somewhat different from that in the case of a patient with rounded abdomen. Using the corresponding means for preventing inadmissible high pressure, an increase in force can now be detected, which indicates that the ultrasound transducer, for example because of the corresponding abdomen rounding, must be raised a little so as to follow the shape of the abdomen without pressing too hard on the patient. That means that in this way it is possible for the ultrasound transducer movement to be adapted specifically to the object to be examined, by the control device continually detecting the force of the pressure or the application force and making corrective adjustments to the control curve, so as to control the physical circumstances according to the transducer movement.

So that the control device knows how the object to be examined is positioned in the room, for practical purposes a device for detecting the position of the object to be examined is provided, whereby the control of the robotic arm is carried out according to the position detection results. Thus in principle, a position detection of the object to be examined is carried out and during the examination, preferably also a movement detection, in order to determine whether the patient moves while the examination is in progress. Based on the results of the detection of the corresponding device, which communicates with the control device that controls the robotic arm, the control device now knows whether the patient is lying on his stomach or back or is turned on his side, etc. According to this information the control device can now control the robotic arm in such a way that said arm also actually travels the movement path in the area that is actually to be examined and using the correct orientation.

Thereby the position detection device can comprise one or several sensors to be arranged on the object to be examined, such as, for example, electromagnetic sensors or ultrasound sensors, wherein the position of the sensors can be detected using a detection device. From the arrangement of the sensors relative to the detection device, if the sensors are arranged at marked object points, the position in space of the objects can be determined exactly. However, it would also be conceivable to use a camera recording the object to be examined together with an assigned image evaluation device. Using this it is also possible to detect the position in space of the patient exactly by evaluating the camera images.

For practical purposes, the ultrasound transducer itself is detachably arranged on the robotic arm so as to give the operator the option to guide the transducer manually as was done previously, if he deems this necessary in rare cases.

The communication of the ultrasound transducer with the control device can be made via a cable link or in a cable-free fashion, for example via an infrared or Bluetooth connection or any other cable free communication option.

Further for practical purposes, there is an interface through which remote control of the ultrasound device is provided, in particular of the movement of the robotic arm, in as far as the latter can be controlled via a manual operating device, as well as a transmission of image data to the location of the remote control. This makes it possible to operate the ultrasound device from a different location, for example in a clinic, with camera monitoring. For example, the corresponding areas or organs are shown to the external operator on the display screen, so that he/she can select the corresponding control curve, as, using for example a joystick or such like, and when there is camera monitoring, he/she can also move the robotic arm or the ultrasound transducer into an optimal start position, on the basis of which the automatic movement operation occurs using the previously selected control curve.

BRIEF DESCRIPTION OF THE DRAWINGS

Further advantages, features and details of the invention arise from the exemplary embodiment described below with reference to the drawing.

The drawing is purely a concept drawing and only reproduces schematically the basic principle of an inventive ultrasound device.

DETAILED DESCRIPTION OF INVENTION

It shows an ultrasound device 1, comprising a device stand 2, in which a control device 3 is arranged, via which, in the example shown, the entire operation of the ultrasound device 1 is controlled. On the device stand 2 there is a robotic arm 4, which, in the example shown, is made up of three arm sections 5, which are joined by corresponding joints 6. On joint 6, shown on the right in the FIGURE, provision is also made for a holder 7 for an ultrasound transducer 8, which is moved over the surface of an object to be examined 9, which is arranged on a patient positioning table 10. The joints 6 are designed in such a way that they allow not only the individual arm sections 5 and possibly the holder 7 to be swiveled, but they also allow pivoting movements, so that there is a plurality of separate degrees of freedom for the arm movement.

The movement of the robotic arm 4 is controlled by the control device 3, which to this end activates corresponding actuators in the joint connections 6, which are not shown in detail here. These are servomotors that perform swing or pivoting movements.

The robotic arm 4 and hence the movement of the ultrasound transducer 8 is controlled using specific control curves $K_A$, $K_B$, $K_C$, ..., which are stored as an assemblage in a corresponding memory 11 of the ultrasound device. Depending on which examination area or which organ of the object to be examined 9 is to be examined, the operator can select the desired control curve K. To this end different examination areas or organs 13 are displayed on a display screen 12, said areas and organs are identified in the example shown by A, B, C, .... Each letter A, B, C, ..., represents a specific examination area or a specific organ, for example, the pancreas, the liver, the kidneys etc. At least one corresponding control curve is allocated to each examination area or organ 13, as is indicated by the corresponding referencing by the index letters in the respective curve K.

Using a screen cursor 14, the operator selects a desired examination area 13. The control device 3 then loads the corresponding control curve K from the memory 11, which control curve describes a predetermined movement path for the ultrasound transducer 8, which path is optimally designed for an optimal take of ultrasound images related to the specific examination area or specific organ to be examined. Using for example a manual control device 15, for example a joystick, the operator moves the ultrasound transducer 8 into a start position, by placing it at a specific position on the object to be examined 9, usually on a patient. This start point is selected by the operator in a manner which is specific to the area to be examined or specific to the organ, i.e., he/she positions the ultrasound transducer 8 in a corresponding area or organ-specific start position. Then by pressing a start button or similar, the robotic arm 4 is automatically controlled by the control device 3 according to the selected control curve 11. The ultrasound transducer 8 then describes the optimized movement path, via which it is ensured that images are taken from all the relevant positions and in all the relevant alignments of the ultrasound transducer 8, which images can then be displayed on the display screen 12.

Further a detection device 16 is provided, with which it is possible to determine exact information relating to the position in space of the object to be examined 9. This detection device 16 communicates with the ultrasound device 1 or the control device 3, which in the process receives information about the actual position of the object to be examined 9. Said object can be lying on its back, on its stomach or on its side, which can be recognized using the detection device 16. In addition, it is possible in the process to detect where the patient is in relation to the patient positioning table, thus where, for example, the head or the feet are situated. This information is used by the control device 3 to allow it to adjust the arm control correspondingly. Corresponding sensors 17 on the robotic arm 4, which are arranged in the region of the joint connection 6, are also used for this. These sensors are means for preventing an inadmissible high exertion of force by the ultrasound transducer 8 on the object to be examined 9. These are for example pressure sensors, which determine what force is acting on the respective joint connection 6. The sensors 17 send their corresponding signals to the control device 3, which can derive from that whether the ultrasound transducer 8 is pressing on the object to be examined 9 with an acceptable force, or whether the force is increasing, for example in the case where the abdomen curves outwards and a horizontal movement would go against the curve of the abdomen. The control device 3 then adjusts the corresponding control curve 11 so as to raise the ultrasound transducer 8 correspondingly and to guide it so that the transducer can also be moved optimally and with essentially constant application force along a three-dimensional curved surface of a patient. The sensors 17 not only serve to determine information about the forces acting on the joint connections 6, but also serve to determine position, path and angle information, which is used by the control device 3 for exact control of the robotic arm 4.

Using the information supplied by the sensors 17, it is also possible to generate the control curves 11. To this end the operator moves the ultrasound transducer 8 into a start position and then travels the optimal movement path by manually moving the activated robotic arm 4 (i.e. not blocked by its servomotors) together with ultrasound transducer 8 along the object to be examined 9. Thereby the control device 3 records all the information supplied by the sensors 17 and thus generates an area or organ-specific control curve K, which is then stored in the memory 11. This control curve can, however, as already described, be adapted and adjusted during the actual image acquisition, if so required by the patient body that is to be examined.

The ultrasound transducer 8 itself must be removed from the holder 7, in order to afford the operator the possibility of also guiding the ultrasound transducer 8 manually as before. The ultrasound transducer 8 communicates with the control device 3 either via a cable 18, or alternatively this can also be a wireless communication, as is indicated by the two antennae 19.

Via an interface 20 there is also the possibility of accessing the ultrasound device 1 externally, consequently, therefore, to control the entire image acquisition operation externally. Through this interface the externally located operator receives all the information on the display screen there, so that he can select corresponding control curves, in addition, he can move the robotic arm 4 manually using a joystick or similar there, just as he can also initiate the examination function and of course the ultrasound images taken are also output to him at his workstation.

In conclusion, it must also be noted that the robotic arm 4 can also be arranged at the patient positioning table 10. Further, the ultrasound device 1 can be a fixed or mobile piece of equipment.

The invention claimed is:

1. An ultrasound device, comprising:
   a robotic arm;
   an ultrasound transducer configured to be moved along an object to be examined, the ultrasound transducer arranged on the robotic arm which freely moves in space, and wherein the robotic arm includes a joint connection and a sensor, wherein the sensor detects forces acting on the joint connection and provides position, path and angle information for controlling the robotic arm;
   a display device for displaying a plurality of examination areas each assigned to a control curve that defines an optimally predetermined movement path for the ultrasound transducer for taking an optimal ultrasound image related to a respective examination area;
   a selection device for selecting a desired examination area to be examined from the plurality of examination areas;
   a control device for controlling movement of the robotic arm, the control device communicating with the ultrasound transducer, controlling a transmit and receive mode of the ultrasound transducer and processing ultrasound signals received from the ultrasound transducer, wherein the control device includes a memory device for storing a plurality of control curves, wherein the control device loads a corresponding control curve related to the desired examination area for moving the ultrasound transducer via the robotic arm, wherein when an unacceptable force level due to contact between the ultrasound transducer and the object is detected by the sensor the control device adjusts a corresponding control curve to reduce the force to an acceptable level; and a safety clutch located on the robotic arm for stopping an arm movement of the robotic arm to prevent the unacceptable force level exerted by the ultrasound transducer on the object if the unacceptable force level is detected.

2. The ultrasound device as claimed in claim 1, wherein at least one of the control curves is created from a manual movement of the transducer by an operator of the control device, and wherein the created curve is stored in the memory device.

3. The ultrasound device as claimed in claim 2, wherein the sensor is used to detect the arm movement in order to create the control curve.

4. The ultrasound device as claimed in claim 1, further comprising a joystick in order to manually control the movement of the robotic arm.

5. The ultrasound device as claimed in claim 1,
further comprising a position detection device to detect the position of the object to be examined, and
wherein the robotic arm is controlled as a function of the detected position.

6. The ultrasound device as claimed in claim 5, wherein the position detection device utilizes an object sensor configured to be arranged on the object to be examined, the object sensor locatable by a detection device.

7. The ultrasound device as claimed in claim 5, wherein a camera recording the object to be examined has an assigned image evaluation device.

8. The ultrasound device as claimed in claim 1, wherein the ultrasound transducer is arranged detachably on the robotic arm.

9. The ultrasound device as claimed in claim 1, wherein the ultrasound transducer communicates with the control device via a cable link or in a cable free fashion.

10. The ultrasound device as claimed in claim 1, wherein the robotic arm is arranged on a device stand or on a table on which the object to be examined is configured to be positioned to provide a manual control of the transducer.

11. The ultrasound device as claimed in claim 1, further comprising an interface through which remote control of the ultrasound device is provided by controlling the movement of the robotic arm, the interface further providing a transmission of image data to the location of the remote control.

12. The ultrasound device as claimed in claim 1,
wherein the robotic arm includes a plurality of arm sections, which can be swiveled and/or pivoted relative to each other, and
wherein the robotic arm has at least four degrees of freedom of movement.

13. The ultrasound device as claimed in claim 12, wherein the robotic arm has six degrees of freedom of movement.

* * * * *